United States Patent [19]

Gangadharan et al.

[11] Patent Number: 5,811,107
[45] Date of Patent: Sep. 22, 1998

[54] SKIN CLEANSER

[75] Inventors: Balgopal Gangadharan, Lake Hiawatha, N.J.; Marshall A. Hayward, Weybridge, England

[73] Assignee: SmithKline Beecham Corporation, Phila, Pa.

[21] Appl. No.: 437,478

[22] Filed: May 9, 1995

Related U.S. Application Data

[63] Continuation of Ser. No. 211,005, May 18, 1994, abandoned.

[51] Int. Cl.⁶ .......................... A61K 31/78; A61K 31/79
[52] U.S. Cl. .......................... 424/401; 424/59; 424/489; 514/844; 514/845; 514/846; 514/847; 514/848
[58] Field of Search .......................... 424/59, 401, 489; 514/844, 845, 846, 847, 848

[56] References Cited

U.S. PATENT DOCUMENTS

| | | | |
|---|---|---|---|
| 3,645,904 | 2/1972 | Beach | 252/89 |
| 3,708,435 | 1/1973 | Starkman | 252/544 |
| 4,126,142 | 11/1978 | Saute | 132/7 |
| 4,508,634 | 4/1985 | Elepano et al. | 252/163 |
| 4,586,962 | 5/1986 | Barabas | 134/4 |
| 4,743,442 | 5/1988 | Raaf et al. | 424/47 |
| 4,752,472 | 6/1988 | Kligman | 424/59 |
| 4,963,591 | 10/1990 | Fourman et al. | 514/944 |
| 4,965,071 | 10/1990 | Kawan | 424/401 |
| 5,019,174 | 5/1991 | Wallach | 134/40 |
| 5,139,770 | 8/1992 | Shih et al. | 424/59 |
| 5,143,071 | 9/1992 | Keusch et al. | 128/640 |

FOREIGN PATENT DOCUMENTS

| | | |
|---|---|---|
| 0140325 | 5/1985 | European Pat. Off. . |
| 1587321 | 9/1995 | France . |
| 57-207648 | 12/1982 | Japan . |

OTHER PUBLICATIONS

*Soap/Cosmetics/Chemical Specialities*, vol. 58, No. 1, P. 90 (1982).

*Primary Examiner*—Thurman K. Page
*Assistant Examiner*—Sharon Howard
*Attorney, Agent, or Firm*—Nora Stein-Fernandez; Janice E. Williams; Edward T. Lentz

[57] ABSTRACT

This invention relates to a polymer-based cleanser for superficial and deep cleansing of skin.

16 Claims, No Drawings

SKIN CLEANSER

This is a continuation of application Ser. No. 08/211,005, filed May 18, 1994, now abandoned.

This invention relates to a polymer-based cleanser for superficial and deep cleansing of skin.

Area of the Invention

Skin cleaning and treating materials in the form of pastes, viscous suspensions, creams, gels and even plasticized polymeric have long been used, no doubt starting in pre-historic times. Early historical records and anecdotes describe the use of plant and animal derived pastes, gels and appliques which were applied to the skin for medicinal and cosmetic purposes. More recent history reveals a continued interest in topically applied suspensions, gels, pastes and the like which are left on the skin for a discrete period, then peeled or scrubbed off, thereby removing surface and embedded grime and debris.

Hair follicles secrete a horny material through the life of the individual. Normally this material is extruded and removed by washing, shaving or other cleansing processes. Age-related skin changes may interfere with this extrusion process. Follicles may dilate and fill up with horny material which can trap small velus hairs. This accumulated debris distends the follicle resulting in which are commonly called clogged pores, comedones and blackheads. Bacteria such as *P. acnes,* fungi (*P. ovale*) and a mite (*Demodex folliculorum*) contribute to follicular debris build-up. Diseases such as acne, keratosis pilaris, ichthyosis and fungal infections involve abnormal and excessive keratinazation.

It would be desirable to provide an applique which would remove surface and embedded debris without sacrificing skin comfort and which avoids redness, especially that often associated with removing plasticized appliques. This invention provides such an applique. When applied to the skin, these cleansers will adsorb surface sebum, deposited grime and soils and will attach to follicular deposits. Removing the applique removes these topical and embedded soils, grime and debris.

SUMMARY OF THE INVENTION

This invention covers a composition for forming an applique for cleaning or treating skin comprising a lower alcohol or alcohol/water solvent in which is dissolved between 0.1 to 20% by weight/volume of a polymer consisting essentially of a non-acrylate, pre-polymerized high molecular weight, dermatologically acceptable, adhesive polymer. The cleansing is accomplished by applying the formulation to skin as an applique, drying the applique, contacting the dried applique with an adhesive tape type material which bonds with the applique, and then pulling the applique/tape away from the skin.

SPECIFIC EMBODIMENTS

These skin cleansers are based on certain naturally occurring and synthetic polymers which are soluble in simple alcohols, or simple alcohol and water mixtures. It has been found that the selected polymers remove surface and follicular debris when formulated and applied without additives which modify their native configuration. Adding polymerizing agents or cross-linkers to the selected polymers reduces the capacity of these appliques to effectively remove soil. Thus polymers are pre-formed, that is they are not presented as monomers and cross-linked when applied to the skin. They may be polymerized just prior to use by mixing monomers and cross-linking agents from separate containers, then after polymerization has occurred, applying the resulting polymeric solution to the skin. But polymers are not formed in situ, that is when applied to the skin. These polymers will be dermatologically acceptable within the ambit of their use as skin cleansers.

Polymers include those which have intrinsic adhesive properties and are soluble in simple alcohols or water/simple alcohol mixtures. Useful polymers include PVP, VP/vinyl acetate, alkylvinyl ethers, alkylvinyl ether/maleic acids and acid salts, or carboxymethyl celluloses. The most preferred polymers are PVPs and methylvinyl ether/maleic acid and acid salts sold by International Speciality Polymers of Wayne, N.J., U.S.A. A single polymer, or mixtures, can be used in these formulations.

Forming appliques is a matter of providing a liquid or gel which can be conveniently spread on the skin, which will then quickly dry to an elastic, pliable solid, and which can then be peeled from the skin by some means. The elastic, pliable characteristics are achieved by selecting polymers and polymer mixtures which provide these characteristics. In addition, they should be soluble in solvent with a low vapor pressure so the solvent quickly evaporates when the solution is applied to the skin. Simple alcohols and alcohol/water mixtures are best for this purpose. A simple alcohol is methanol, ethanol or isopropanol. Ethanol is preferred. Methanol may not be useful in certain applications because of its toxicity potential. Pure alcohol may be used as the solvent, though combining water with alcohols is also useful. The solvent may contain up to about 20% water. A preferred alcohol/water mix is one in the range of 90% alcohol/10% water. Another preferred solvent is 95% ethanol/5% water.

Formulations of polymer and solvent will have some degree of viscosity so that when one goes to apply them to the skin they will not flow excessively. It is most desirable to provide an out-of-the-bottle formulation which forms up in the manner of a gel or paste which can be readily spread with the fingers or a pliable device. While it is expected that the polymers at the concentrations used to make these cleansers will impart such qualities, an agent to thicken may be added to a formulation which inherently does not have this property.

Polymer concentrations will range from about 0.1 to 20 percent by weight (weight/volume). Within this range the concentration can be infinitively varied. A more preferred range is between about 2–10%, and most formulations will contain about 5% polymer.

Solutions are readily prepared by adding a selected amount of polymer to solvent with stirring or mixing means. This can be done at room temperature, or at slightly elevated temperatures if desired.

To clean skin, a dollop of liquid or gel is placed on the skin and spread into an applique by hand or a soft pliable device. For example, a small amount of material is dispensed onto the fingers and spread over the cheek or the face. Body heat, air flow and ambient heat will evaporate the solvent leaving behind an elastic, pliable essentially dry applique. This should take several minutes, e.g., 3–10, after which the applique can be removed. This is accomplished by pulling it off; simply grasp the edge of the applique with the fingers and steadily pull it from the face. An alternative, and preferred method is to take a piece of adhesive tape, or similar material, and touch it to the dried applique. Both are then pulled from the skin with steady, gentle pressure.

Adhesive tape refers to any cloth or plastic patch or strip which has an adhesive coating which sticks to the applique well enough to pull it from the skin. Preferred materials are the Scotch™ tapes sold by 3M Company of Minneapolis, Minn., U.S.A., medical adhesive tapes and patches like Blenderm™ also manufactured by 3M Company and Dermiclear™ manufactured by Johnson & Johnson. Preferred adhesives are hypoallergenic acrylics.

The following examples are given to illustrate the invention, not to limit its scope. Reference is made to the claims for what is reserved to the inventors hereunder.

EXAMPLE 1

Applique Formulation

A high molecular weight PVP (Plasdone K 120, MW~2 million) was dissolved in USP ethanol (typically containing 4 to 5 percent water by weight) at the five percent level (weight/volume). This was accomplished by dispensing 5.0 grams of polymer into 100 grams of USP ethanol under high speed stirring (2000 RPM) at room temperature. Polymer was slowly added into the vortex of the ethanol to prevent clumping. Stirring was terminated when dissolution of the polymer was complete.

A portion of this ethanolic solution was applied to the nose with the fingers and allowed to dry completely (5–7 minutes). Then a length of Scotch tape was applied to the surface of the dried applique. Tape and adhered polymer were peeled away from the skin. When the tape was examined under a microscope (Power x100) several layers of stratum corneum and hair follicles encased by horn were observed.

What is claimed is:

1. A composition for forming a peel-off applique for cleaning or treating skin comprising a lower alcohol or alcohol/water solvent in which is dissolved between 0.1 to 20% by weight/volume of a polymer consisting essentially of a non-acrylate, pre-polymerized high molecular weight, dermatologically acceptable, adhesive polymer or monomer which is polymerized just prior to use, said polymer or polymerized monomer having intrinsic, adhesive properties and having solubility in simple alcohols or water/simple alcohol mixtures.

2. A composition according to claim 1 where the polymer is polyvinyl pyrrolidone (PVP), PVP/vinyl acetate or where the polymer is derived from alkylvinyl ethers, alkylvinyl ether/maleic acids and acid salts, or carboxymethylcelluloses.

3. A composition according to claim 2 where the solvent is an alcohol/water mixture where the alcohol is methanol, ethanol or isopropanol.

4. A composition according to claim 3 where the polymer is PVP having a molecular weight of about 2 million.

5. A composition according to claim 3 where the polymer is methylvinyl ether/maleic anhydride having a molecular weight between 18,000 and 80,000.

6. A composition according to claim 3 where the polymer is polyethylene oxide.

7. A composition according to claim 3 where the polymer is PVP/vinyl acetate.

8. A composition according to claim 4 where the PVP polymer is at a 5% concentration in ethanol.

9. A method for cleansing skin which comprises:

a. applying to the skin a peel-off formulation comprising a lower alcohol or alcohol/water solvent in which is dissolved between 0.1 to 20% by weight/volume of a polymer consisting essentially of a non-acrylate, pre-polymerized high molecular weight, dermatologically acceptable, adhesive polymer or monomer which is polymerized just prior to use, said polymer or polymerized monomer having intrinsic adhesive properties and having solubility in simple alcohols or water/simple alcohol mixtures;

b. allowing the formulation to dry to form an applique;

c. contacting the dried applique with an adhesive tape material which bonds with the applique; and d. removing the applique by pulling the tape with the bound applique away from the skin.

10. The method of claim 9 where the polymer is polyvinyl pyrrolidone (PVP), PVP/vinyl acetate or where the polymer is derived from alkylvinyl ethers, alkylvinyl ether/maleic acids and acid salts, or carboxymethylcelluloses.

11. The method of claim 10 where the solvent is an alcohol/water mixture where the alcohol is methanol, ethanol or isopropanol.

12. The method of claim 11 where the polymer is PVP having a molecular weight of about 2 million.

13. The method of claim 11 where the polymer is methylvinyl ether/maleic anhydride having a molecular weight between 18,000 and 80,000.

14. The method of claim 11 where the polymer is polyethylene oxide.

15. The method of claim 11 where the polymer is PVP/vinyl acetate.

16. The method of claim 9 which results in removing comedones.

* * * * *

UNITED STATES PATENT AND TRADEMARK OFFICE
CERTIFICATE OF CORRECTION

PATENT NO. : 5,811,107
DATED : September 22, 1998
INVENTOR(S) : Balgopal Gangadharan et al.

It is certified that error appears in the above-identified patent and that said Letters Patent is hereby corrected as shown below:

Title page,
Item [63], Related U.S. Application Data, after "abandoned" and before the period ("."), insert -- , which is a 371 national phase application of international application No. PCT/US92/07695, filed September 11, 1992, and published as WO 93/05893 on April 1, 1993, which is a continuation of application Serial No. 07/762,692, filed September 19, 1991, now abandoned --.

Column 1,
Line 4, after "abandoned" and before the period ("."), insert -- , which is a 371 national phase application of international application No. PCT/US92/07695, published April 1, 1993, which is a continuation of application Serial No. 07/762,692, filed September 19, 1991, now abandoned --.

Signed and Sealed this

Fifth Day of August, 2003

JAMES E. ROGAN
*Director of the United States Patent and Trademark Office*